United States Patent
Benveniste et al.

(10) Patent No.: US 6,541,978 B1
(45) Date of Patent: Apr. 1, 2003

(54) METHOD, SYSTEM AND DEVICE FOR PRODUCING SIGNALS FROM A SUBSTANCE BIOLOGICAL AND/OR CHEMICAL ACTIVITY

(75) Inventors: Jacques Benveniste, Paris (FR); Didier Guillonnet, Cagnes-sur-mer (FR)

(73) Assignee: Digibio, Paris (FR)

( * ) Notice: Subject to any disclaimer, the term of this patent is extended or adjusted under 35 U.S.C. 154(b) by 0 days.

(21) Appl. No.: 09/787,570
(22) PCT Filed: Sep. 23, 1999
(86) PCT No.: PCT/FR99/02270

§ 371 (c)(1),
(2), (4) Date: Jul. 18, 2001

(87) PCT Pub. No.: WO00/17638
PCT Pub. Date: Mar. 30, 2000

(30) Foreign Application Priority Data

Sep. 23, 1998 (FR) .............................. 98 12058

(51) Int. Cl.[7] .............................. G01V 3/08; G01V 3/10
(52) U.S. Cl. ........................................ 324/329; 324/441
(58) Field of Search ................................ 324/239, 441, 324/232, 210, 226, 262, 204, 71.1, 663, 692, 668; 340/627, 631; 436/66, 627

(56) References Cited

U.S. PATENT DOCUMENTS

| 4,095,168 | A |   | 6/1978  | Hlavka           |        |
|-----------|---|---|---------|------------------|--------|
| 4,692,685 | A | * | 9/1987  | Blaze ........... | 324/61 |
| 5,583,432 | A |   | 12/1996 | Barnes           |        |
| 5,752,514 | A |   | 5/1998  | Okamura et al.   |        |
| 6,196,057 | B1| * | 3/2001  | Discenzo ....... | 73/54.01|

FOREIGN PATENT DOCUMENTS

| WO | 94/17406 | 8/1994 |
| WO | 96/08200 | 3/1996 |
| WO | 96/10740 | 4/1996 |

* cited by examiner

Primary Examiner—Edward Lefkowitz
Assistant Examiner—Subhash A Zaveri

(57) ABSTRACT

The invention concerns a method, a system and a device for producing, from a substance, electric signals characteristic of the biological activity of an active element contained in the substance. The method consists in: placing the substance in a zone subjected to a specific electric, magnetic and/or electromagnetic excitation field. The method further includes a step which consists in transforming the fields resulting form the interaction between the specific excitation filed and the substance, into signals, in particular electric signals, using a first transducer receiving the resulting fields.

45 Claims, 6 Drawing Sheets

Figure 1:
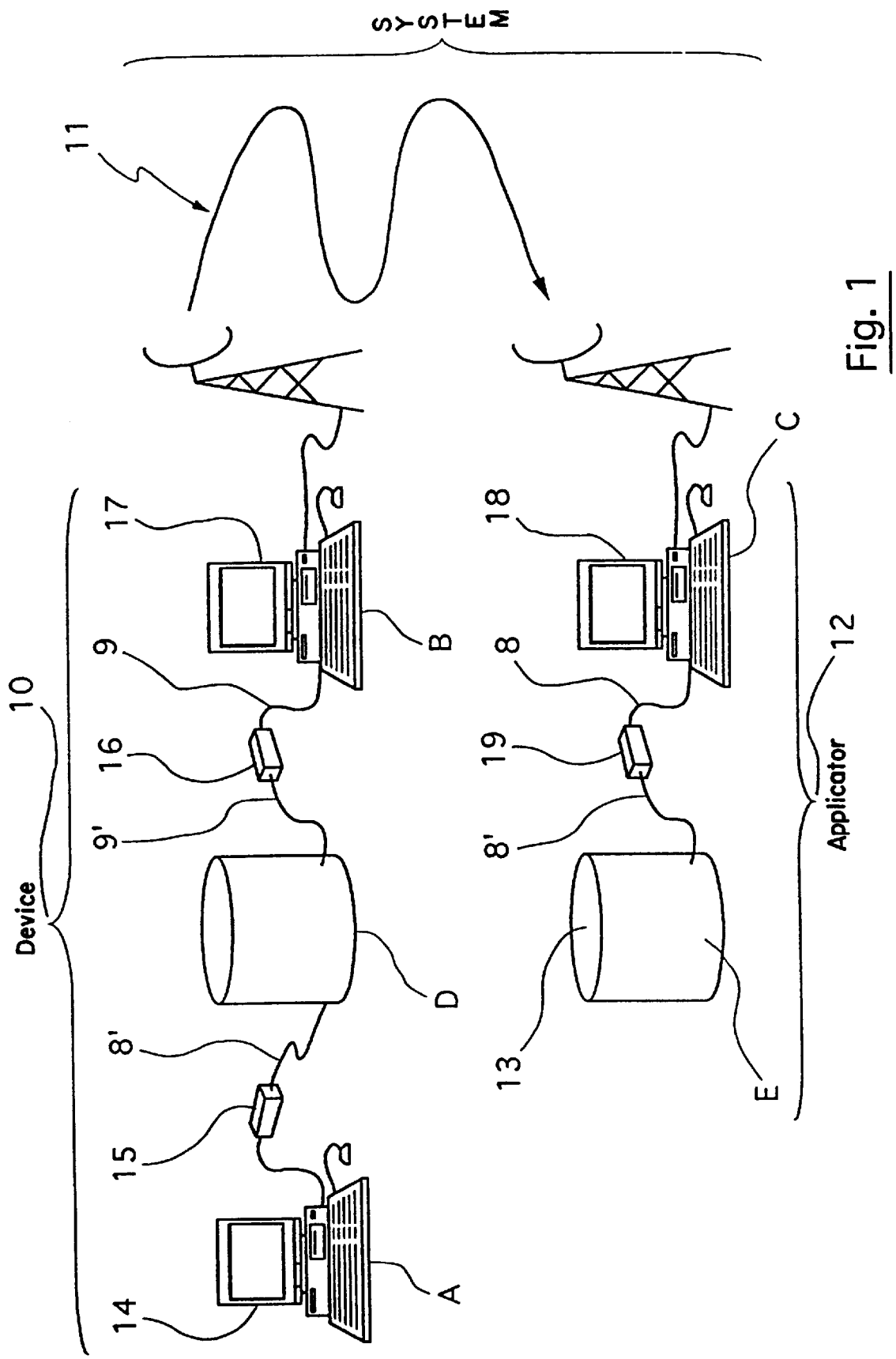

METHOD, SYSTEM AND DEVICE FOR PRODUCING SIGNALS FROM A SUBSTANCE BIOLOGICAL AND/OR CHEMICAL ACTIVITY

The present invention relates to a method, a system and a device for producing signals from a substance, in particular electric signals, characteristic of the biological and/or chemical activity or the biological and/or chemical behaviour of said substance or an active element contained in said substance. The invention also relates to a method and a system for controlling said signals. The invention also relates to the applications of said method, system and device in particular to the production of active substances and to the detection of defined substances. Finally, the invention relates to signals linked to a biological and/or chemical activity thus produced by said method, system and device.

It is known from the research works of Jacques Benveniste, in particular those described in the patent application WO 94/17406 published on Aug. 4, 1994, that one can pick up, from a biological and/or chemical active element such as a chemical compound, a cell or a micro-organism, or from a substance containing this active element such as a purified preparation, a biological sample, or a living being, an "electromagnetic signal characteristic of the biological and/or chemical activity or of the biological and/or chemical behaviour" of said substance and/or said active element contained in said substance.

It is also known that it is possible to transform, in particular by means of a transducer, such an electromagnetic signal into electric signals. In the following text one also means by "electric signals characteristic of the biological and/or chemical activity or of the biological and/or chemical behaviour of said substance or of an active element contained in said substance" the electric signals derived by signal digitising and/or processing. In this expression the word "characteristic" is used in the meaning where the physical parameters of the electric signals are specific to the substance or to the active element contained in said substance and that the application of these electric signals, via a transducer, to a biological control system makes it possible:

(i) to induce a biological and/or chemical activity on said biological control system relative to that of the substance of origin or the active element it contains;

(ii) to reveal a characteristic of the substance or the active element it contains, at the origin of said electric signals.

The patent application WO 94/17406 published on Aug. 4, 1994, describes a method and a device for picking up "an electromagnetic signal characteristic of a biological and/or chemical activity or of a biological and/or chemical behaviour" from a biological and/or chemical active element such as a chemical compound, a cell or micro-organism, o r from a substance containing this active element such as a purified preparation, a biological sample, or a living being.

Since then the inventors have discovered that it is possible to improve the quality of the electromagnetic signal picked up as well as the reliability of the method for producing these signals and that consequently it is possible to produce characteristic electric signals appropriate for industrial applications. The production of such characteristic electric signals implies an exceptional industrial importance.

It thus becomes possible to detect and characterise active elements present in low concentration or in very low concentration in a substance. As examples, it is thus possible to monitor the presence or absence of chemical compounds such as caffeine, ionophoretic-calcium, ovalbumin, propranolol or micro-organisms such as bacterium coli, streptococci, staphilocci whose presence is looked for.

It thus becomes possible to carry out remote tests at several thousands of kilometers since the characteristic signals are electric signals which can immediately be transmitted to the investigation centre of the control laboratory.

It is possible to modify the biological and/or chemical activity or the biological and/or chemical behaviour of a biological receptor system by submitting it to the effects of characteristic electric signals. It also becomes possible to produce new drugs such as solutions depending on signals from arnica, bradykinin, caffeine, nicotine. New production techniques for drugs can be implemented. For example, in the case of certain drugs such as antibiotics, anti-viruses, anti-parasites, anti-mitotics which, to act within bacteria, viruses or cells (tumour cells in particular), must breach the defensive barriers of the above, the signals of these drugs are applied directly into the heart of the bacteria, viruses or cells. In fact, the application of characteristic electric signals, via a n appropriate transducer, generates magnetic fields which penetrate into the bacteria, viruses or cells and modify their chemical and/or biological behaviour.

It is possible to store the characteristic electric signals in data banks, using computer techniques. Then, the spread of therapeutic resources, from one point to the other on the planet, is instantaneous according to needs.

The examples described above concern the medical domain. The chemical industry also, such as electronic components, will also be concerned by the new possibilities offered by the present invention. The use of electromagnetic fields, emitted by characteristic electric signals, to modify the behaviour of molecules and promote chemical reactions will open up new prospects concerning both the conception of new materials and their methods of production. Thus, for example, it will be possible to use them as catalysts able to influence the stereochemistry of molecules.

The method according to the invention making it possible to improve the performances of characteristic electric signals comprises the stages:

of placing said substance in a zone submitted to a specific excitation field of electric, magnetic and/or electromagnetic nature, of transforming the fields resulting from the interaction of the specific excitation field and the substance, into signals, in particular electric signals, by means of a first transducer receiving said resulting fields.

In fact, the inventors have noted that, in a surprising manner, the use of an excitation field such as for example an electromagnetic field of uniform power spectral density over a frequency spread (for example white noise of 1 Hz to 20 kHz) makes it possible to improve the performance of characteristic electric signals. As an example of such a first transducer, one can mention very sensitive small copper wire bobbins with an impedance of 300 Ohms; internal diameter of 6 mm, external diameter of 16 mm, length 6 mm, normally used as telephone receivers.

Preferably, the process according to the invention further comprises the stage for processing said signals derived from said first transducer, relative to second signals derived from a second transducer receiving the specific excitation field, in the absence of said substance. As an example, the processing can consist of subtracting these two signals by using two receiver bobbins connected in series and with opposite phases, one facing said substance and receiving the electromagnetic field through said substance and the other receiving the electromagnetic field directly. Thus, the part of the signals really characteristic of the biological and/or chemical activity or of the biological and/or chemical behaviour of said substance or said active element contained in said substance, is enhanced relative to that derived from the first transducer alone.

As an example, according to another embodiment of the invention, the processing can consist of recording consecutively the signals coming from said substance and then the signals coming from a neutral substance (water or physiological serum), then subtracting the first signals from the second (which serve as reference), this subtraction being carried out before or after processing the signals as described below (subtraction of amplitudes or power spectral densities).

Preferably, according to another embodiment of the invention, the process according to the invention comprises the stage of processing the signals derived from said first transducer, in function of the characteristics of the specific excitation field. For example, the signal processing consists of calculating the power spectral density using a Fourier transform, to narrow the useful frequency band (bandpass filter), to normalise the specific excitation field relative to the power spectral density, and to reconstitute a signal using an inverse Fourier transform. As in the case of the preceding embodiment, the part of the signals which are really characteristic of the biological and/or chemical activity or of the biological and/or chemical behaviour of said substance or said active element contained in said substance, are thus enhanced relative to that produced without processing.

Preferably, the specific excitation field has the characteristic of having a uniform power spectral density over a frequency band. As an example, the power spectral density is uniform over a frequency band from 1 Hz to 20 kHz. Thus, said substance is submitted to a neutral excitation field of the white noise type.

Preferably, furthermore, the zone submitted to the specific excitation field is insulated from parasitic fields from the environment.

The invention also relates to the applications of the signals produced. To this effect, the method further comprises the stage of applying said signals from said first transducer to a biological receiver, by means of a third transducer. In the case where said signals are processed, it is the signals processed in this way which are applied to the biological system receptor.

As an example, said third transducer will generate and emit an electromagnetic field in the direction of biological system receptors such as a carrier substance or a reactive medium producing stereochemical molecules. This electromagnetic field will modify the biological and/or chemical activity or the biological and/or chemical behaviour of the biological system receiver as a function of the nature of biological and/or chemical activity or the biological and/or chemical behaviour of said substance. Thus, for example, it is possible to send the message for caffeine into a water-based beverage to produce a dietetic drink or an alimentary supplement.

The invention also concerns the control of characteristic electric signals. For this, the process further comprises the stage for controlling the correlation between on the one hand, the signal derived from said first transducer or the processed signal and, on the other hand, the biological and/or chemical activity or the biological and/or chemical behaviour of said substance or said active element contained in said substance. This control is carried out by applying, by means of said third transducer, the signals derived from said first transducer to a biological control system and by verifying that said biological control system reacts in a specific manner to the signals from said first transducer. In the case where said signals are processed, it is the signals thus processed which are applied to said biological control system. The reaction of said biological control system must be related to the nature of the biological and/or chemical activity or the biological and/or chemical behaviour of said substance or said active element contained in said substance whose signals are emitted from said first transducer. As an example, in particular one can cite as a biological control system: an isolated guinea-pig heart, a ligand/receptor couple in particular an antigen/antibody couple, the skin of a guinea-pig or a live rabbit which is submitted to a cutaneous injection test, isolated or cultured cells.

Surprisingly, it was noted that the method according to the invention for producing characteristic signals delivers exploitable signals from an active substance whose active element can even be contained in low or very low concentrations (less the $10^6$ moles per liter). The method according to the invention can thus be applied to characterise the presence of an active element at the trace level in a substance.

The invention also relates to a system for producing signals, in particular electric signals, characteristic of the biological and/or chemical activity or of the biological and/or chemical behaviour of a substance or an active element contained in said substance. The invention also concerns a system for implementing the properties of said signals. Said system comprises an emitter generating a specific excitation field of electric, magnetic and/or electromagnetic nature in a zone where said substance is located. As an example, one can cite an emitter with the following characteristics: bobbin with internal diameter 50 mm, length 80 mm, R=3.6 ohms, 3 layers of 112 turns of copper wire, field on the axis to the centre 44 Oe/A, and on the edge 25 Oe/A. Said system also comprises a first transducer receiving the fields resulting from the interaction of said specific excitation field and said substance, said first transducer transforming said resulting fields into signals, in particular electric signals. As an example, one can cite a transducer such as a very sensitive little bobbin of copper wire with an impedance of 300 Ohms, of internal diameter 6 mm external diameter 16 mm, length 6 mm, usually used for telephone receivers. In the case of this example the characteristics of the electric signals derived from the transducer are as follows: amplitude of about 200 mV crest to crest.

Said system also comprises means of emission for applying said signals derived from said first transducer to a biological system receptor. As an example of such means of emission, one can cite a transducer with the following characteristics: bobbin with internal diameter 50 mm, length 80 mm, R=3.6 ohms, 3 layers of 112 spirals of copper wire, field on the axis to the centre 44 Oe/A, and on the edge 25 Oe/A. Examples of biological receptor systems have been mentioned above.

Preferably, the system according to the invention further comprises means for processing said signals derived from said first transducer, in function of the signals derived from a second transducer receiving the specific excitation field, in the absence of said substance. Thus said processed signals are more characteristic of the biological and/or chemical activity or the biological and/or chemical behaviour of said substance or said active element contained in said substance.

Preferably, according to another variant of the invention, the system further comprises means for processing the signals derived from said first transducer, in function of the characteristics of the specific excitation field. In the case of this variant embodiment also, said processed signals are more characteristic of the biological and/or chemical activity or of the biological and/or chemical behaviour of said substance or said active element contained in said substance.

Preferably, said specific excitation field has the characteristic of having a uniform power spectral density over a frequency band.

Preferably, the system according to the invention further comprises means for isolating said zone from parasitic fields from the environment.

Preferably, the system according to the invention further comprises control means for controlling the correlation between, on the one hand, the signal derived from said first transducer or the processed signal and, on the other hand, the biological and/or chemical activity or of the biological and/or chemical behaviour of said substance or said active element contained in said substance. Said control means comprise a third transducer applying the signals derived from said first transducer to a biological control system. In the case where the signals are processed, it is the processed signals which are applied to the biological control system. Said control means further comprise means for verifying that the biological control system reacts in a specific manner to the signals derived from said first transducer, according to the nature of the biological and/or chemical activity or of the biological and/or chemical behaviour of said substance or said active element contained in said substance from which the signals derived from said first transducer are issued. As an example, one can cite as biological control system: an isolated guinea-pig heart, a ligand/receptor couple in particular an antigen/antibody couple, an injectable substance provoking cutaneous reactions, isolated or cultured cells.

Preferably, the system according to the invention is such that said substance contains a low concentration or very weak concentration of an active element.

The invention also relates to a device for producing signals, in particular electric signals, characteristic of the biological and/or chemical activity or of the biological and/or chemical behaviour of a substance or an active element contained in said substance. Said device comprises an emitter generating a specific excitation field of electric, magnetic and/or electromagnetic nature in a zone where said substance is located. It also comprises a first transducer receiving the fields resulting from the interaction of said specific excitation field and said substance. Said first transducer transforms said resulting fields into signals, in particular electric signals. Said signals are characteristic of the biological and/or chemical activity or of the biological and/or chemical behaviour of said substance or said active element contained in said substance.

The device according to the invention further comprises means for processing said signals derived from said first transducer, relative to the signals derived from a second transducer receiving the specific excitation field, in the absence of said substance.

According to another embodiment variant of the invention the device further comprises means for processing the signals derived from said first transducer, in function of the characteristics of the specific excitation field.

Preferably, said specific excitation field has the characteristic of a uniform power spectral density over a frequency band.

Preferably, the device according to the invention further comprises means for isolating said zone from parasitic fields from the environment.

The invention also relates to the applications of the method, system or the device described above. More particularly, the invention concerns the production of active substances in particular the production of drugs. Said active substances are produced by applying said signals derived from said first transducer to a carrier substance. In the case where said signals are processed, it is the signals thus processed which are applied to the carrier substance.

The invention also relates to the application of the process, system or device which has the aim of establishing a table of correlation between the characteristics of a determined substance or an active element contained in said determined substance and the modifications they can induce on test biological systems. Such correlation tables also enter into the framework of the invention, as well as the use of such correlation tables for detecting said determined substance or said active element contained in said determined substance. This detection can in particular be carried out remotely, after transmitting said characteristic signal to a testing laboratory possessing test biological systems. The correlation tables can also be used for controlling the production of homeopathic products, by making it possible to verify the activity of the latter during successive phases of dilution.

The invention also relates to electric signals linked to a biological and/or chemical activity, obtained through implementing the method, the system or the device according to the invention. It is possible to characterise these signals from the effects they produce on a biological control system like that described above.

Figure 1A:
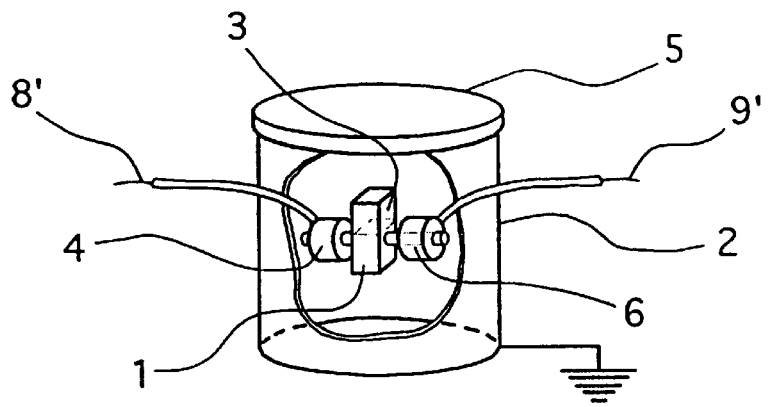
Figure 1B:
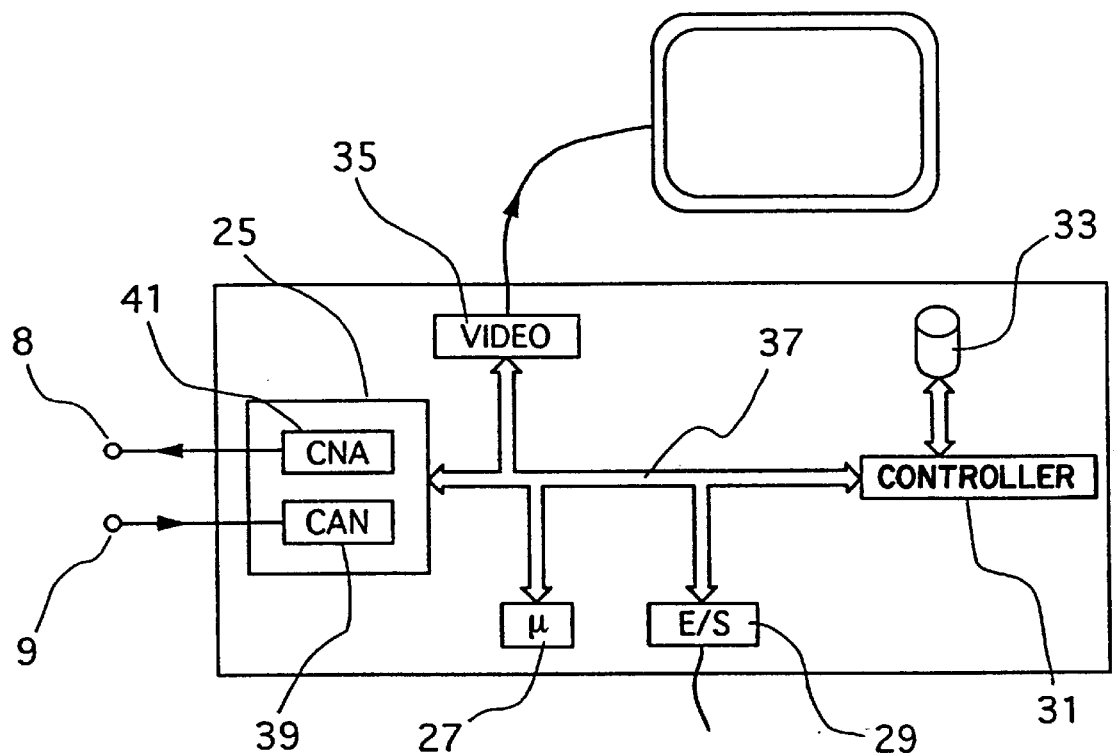

Other characteristics and advantages of the invention will become clear by reading the description of the variants of embodiments of the invention, given as indicative but non-limiting examples, and also by reading the examples of experiments making it possible to validate the method of production of characteristic electric signals, the aim of the present invention, and which refer to the attached drawings in which:

FIG. 1 shows a diagram of an example of an embodiment of a system and a device for producing characteristic electric signals, said system comprising an applicator making it possible to apply the characteristic signals to a biological system receptor, FIG. 1a shows a detailed view in perspective of a part of the device for producing electric signals, showing the emitter of the excitation field and the transducer receiving the resulting fields, FIG. 1b shows in diagrammatic form the type of microcomputer used either for generating the excitation fields, or for recording and transmitting under digitised form the characteristic electric signals, or for applying the characteristic electric signals to biological system receivers via transducers.

Figure 1C:
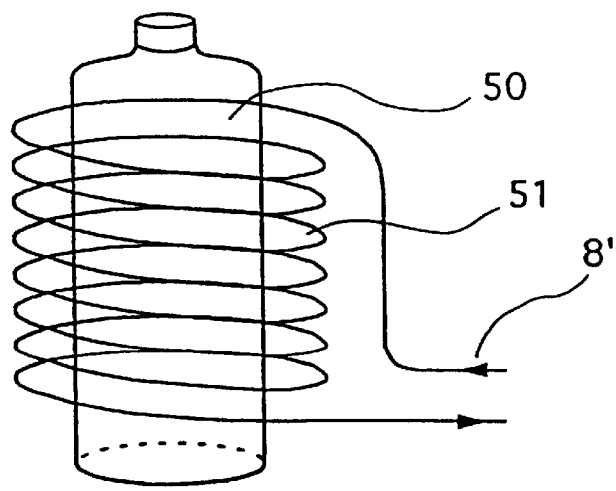
Figure 2:
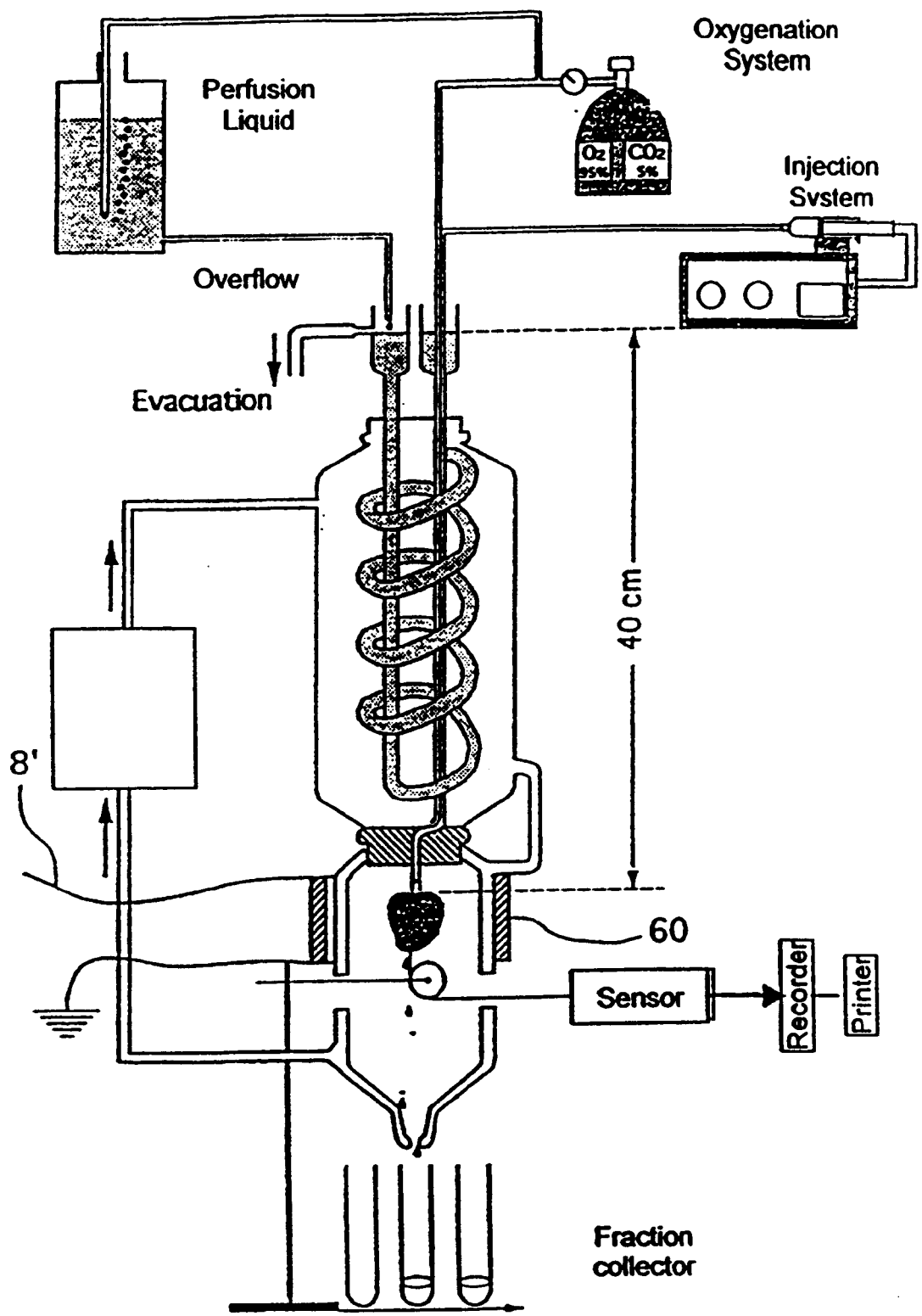
Figure 3:
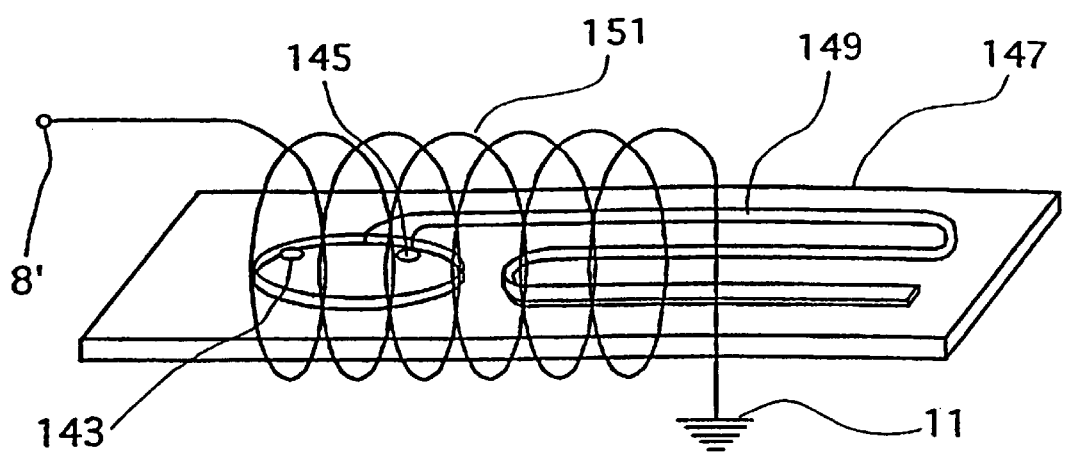

FIG. 1c shows a detailed view in perspective of a part of the applicator intended to apply the characteristic electric signals to biological system receptors, FIG. 2 shows a drawing of an example of an embodiment of an applicator making it possible to control the presence of the characteristic electric signals issued from a solution of acetylcholine by applying them to a biological control system constituted by an isolated perfused guinea-pig heart, FIG. 3 shows a drawing of an example of an embodiment of an applicator making it possible to apply the characteristic electric signals issued from a solution containing as active biological element, *Escherichia coli* K1, Streptococcus or an antibody directed against the polysaccharidic antigen of *Escherichia coli* K1.

Figure 3A:
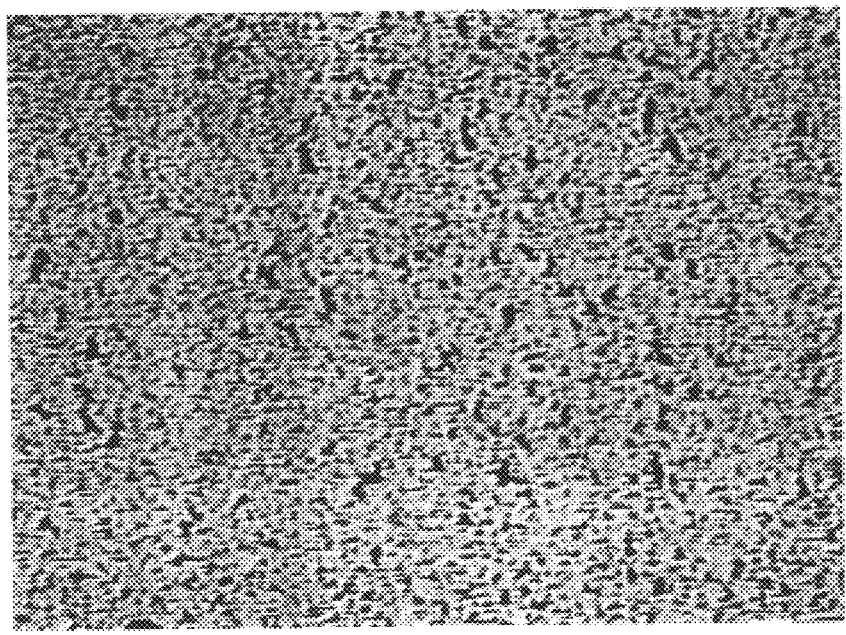
Figure 3B:
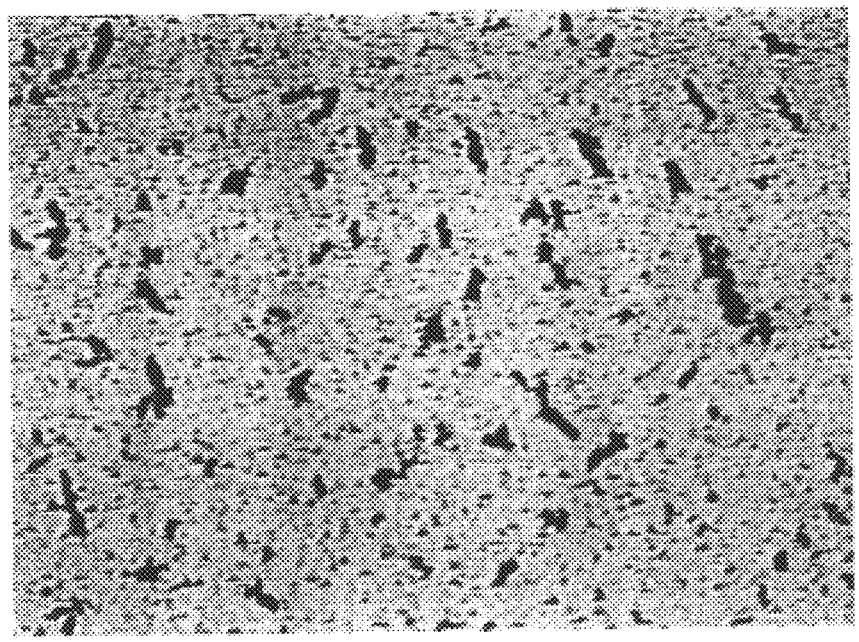
Figure 3C:
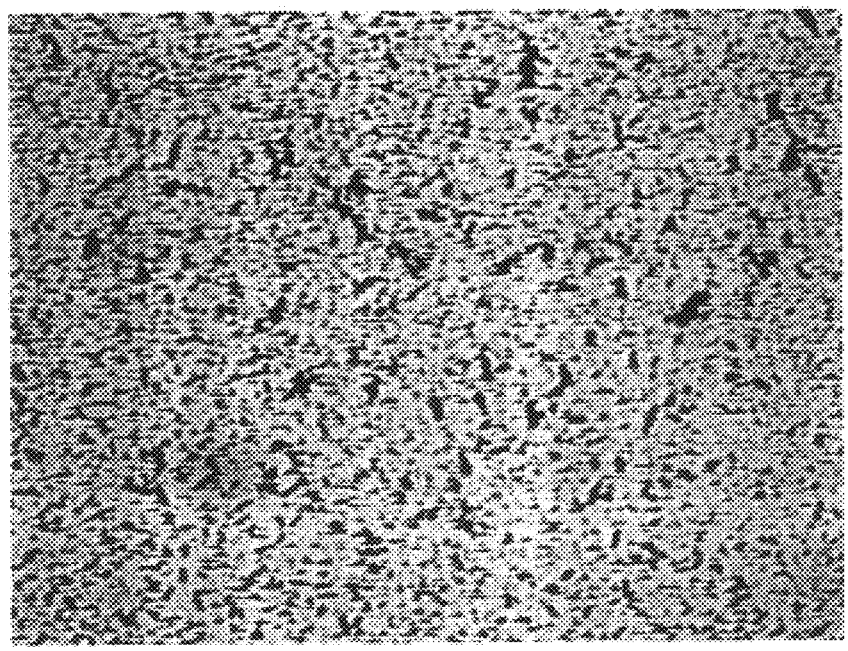
Figure 3D:
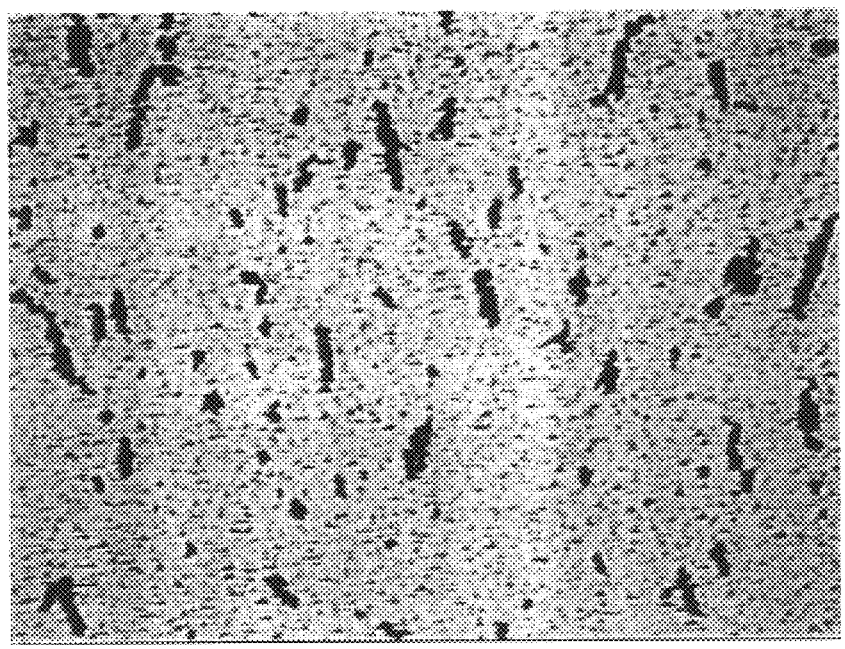

FIG. 3a shows a black and white image of 320 pixels×240 pixels of precipitates formed during the precipitation reaction between the polysaccharidic antigen of *Escherichia coli* K1 and an antibody directed against this antigen, after application of characteristic electric signals coming from a biological system containing *Streptococcus*, FIG. 3b shows a black and white image of 320 pixels×240 pixels of precipitates formed during the precipitation reaction between the polysaccharidic antigen of *Escherichia coli* KP1 and an antibody directed against this antigen, after application of characteristic electric signals coming from a biological system containing *Escherichia coli* K1, FIG. 3c shows a black and white image of 320 pixels×240 pixels of precipitates formed during the precipitation reaction between the polysaccharidic antigen of *Escherichia coli* K1 and an antibody directed against this antigen, after simultaneous application of characteristic electric signals coming from a biological system containing *Streptococcus* and coming from a biological system containing *Escherichia coli* K1, FIG. 3d shows a black and white image of 320 pixels×240 pixels of precipitates formed during the precipitation reaction between the polysaccharidic antigen of *Escherichia coli* K1 and an antibody directed against this antigen, after simultaneous application of characteristic electric signals coming from a biological system containing *Escherichia coli* K1, and coming from a biological system containing a n antibody directed against *Escherichia coli* K1.

Figure 4:
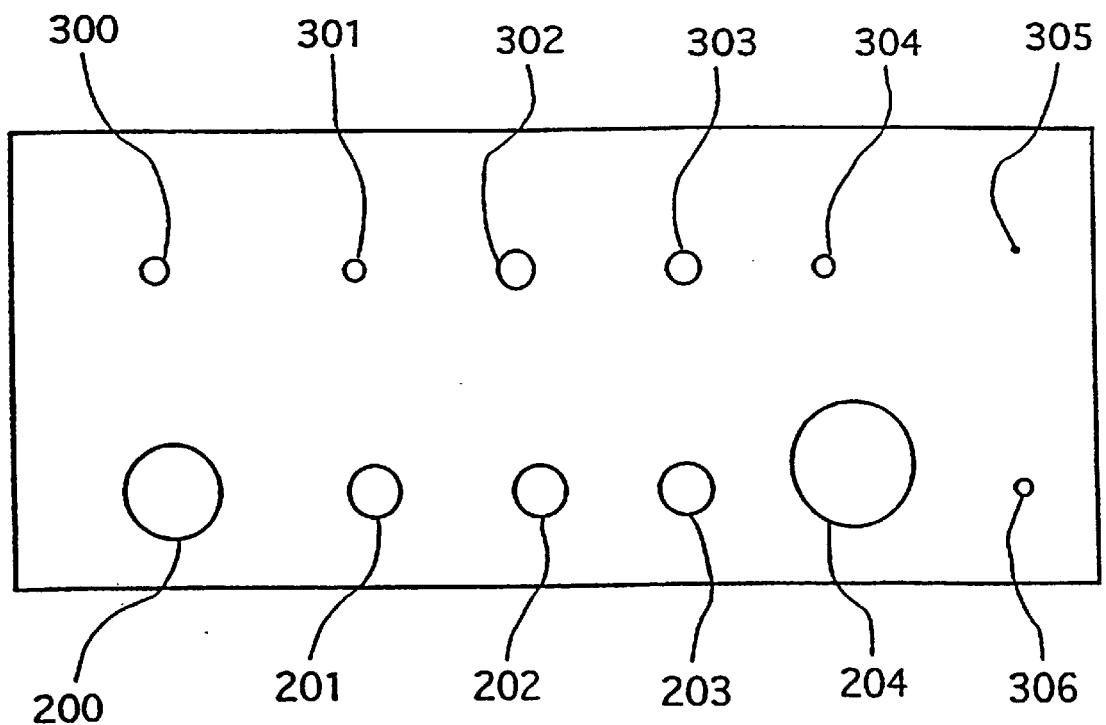

FIG. 4 shows an image of the sub-cutaneous allergic reaction of a skin of a guinea-pig after injection of 0.1 ml distilled water, the distilled water having previously been submitted to an applicator of characteristic electric signals coming from a neuromediator such as acetylcholine (ACh).

Below is described an example of an embodiment of a system and of a device for producing characteristic electric signals, with reference to FIGS. 1, 1a, 1b and 1c. In these figures, a schematic drawing is given of a variant of an embodiment of a system making it possible to produce characteristic electric signals and to implement them for industrial purposes. The signals are characteristic, in the meaning of the present invention, of the biological and/or chemical activity or of the biological and/or chemical behaviour of a substance.

The system comprises a device 10 for producing electric signals characteristic of the biological and/or chemical activity or of the biological and/or chemical behaviour of a substance 1 or of an active element contained in said substance. In the case of the variant described with reference to FIGS. 1, 1a, 1b, 1c, said substance 1 is a solution of caffeine $10^{-6}$ M.

The device 10, located in Paris, for example, produces characteristic electric signals which are digitised after digital-analog conversion. The signals thus digitised are, in a known manner, transmitted remotely, for example by a computer communication network of the Internet type using radio links 11. The digitised signals thus transmitted are received by an applicator 12, located in New York for example, comprising 10 emission means 13. The emission means 13 make it possible to apply the characteristic signals (after digital-analog conversion) to a biological system receptor. In the case of the embodiment described with reference to FIG. 1, 1a, 1b and 1c, the biological system receptor is a dietetic beverage. The digitised signals can be processed 27, recorded and stored 33, before their remote transmission and/or before having been applied to a biological system receiver.

The device for producing the signals 10 comprises a chamber 2 provided with electric and magnetic shielding isolating it from parasitic fields from the environment. The shielded cylindrical chamber is composed of three superposed layers: copper, soft iron, permalloy, made from sheets 1 mm thick. The chamber has an internal diameter of 65 mm, and a height of 100 mm. The chamber is closed by a shielded lid 5. An emitter 4 is situated inside the chamber. It generates a specific excitation field of electromagnetic nature. The emitter is supplied by a generator, 14. In the chamber 2 is placed a glass container 3 with the dimensions 10 mm×10 mm×4.5 mm. This container 3 holds 1 ml of the substance 1. The emitter 4 comprises a bobbin advantageously completed by a magnetic core in soft iron. The emitter bobbin 4 has an impedance of 300 ohms, an internal diameter of 6 mm, an external diameter of 16 mm, and a length of 6 mm. The magnetic core in soft iron is placed in contact with the external walls of the container 3. Said substance is thus submitted to an excitation field emitted by the emitter 4. The generator 14 is designed to generate a low frequency signal especially square or sinusoidal low frequency signals, of pink noise or, advantageously, white noise. The spectrum of the excitation signal supplying the emitter bobbin 4 corresponds closely to the spectrum of audible frequencies (20 Hz–20,000 Hz). The generator 14 can be a generator of an analog signal of known type, using for example a read-only memory (ROM, PROM, EPROM, EEPROM) containing the digital signal of the desired noise. This memory is linked in a known way to a digital-analog converter. A microcomputer 14 can also b e used, provided with a sound card 25 comprising a digital-analog converter 41. For example, one can use a computer 14 of the PC type, operating under the WINDOWS® 95 operating system from MICROSOFT and comprising, apart from the sound card 25 a microprocessor 27, an input/output interface 29, a controller 31 for mass storage 33 and a video interface 35 linked by one or several bus 37. The digital-analog converter 41 of the sound card 25 comprises an output terminal 8. The output terminal 8 of the sound card of the microcomputer 14 is linked to the input terminal 8' of the emitter 4, via an amplifier 15 whose specifications are the following: passband from 10 Hz to 20 kHz, gain 1 to 10, input sensitivity +/−1 V. Among the sound cards 25 which can be used, one can cite, for example the Soundblaster 16 card sold by the CREATIVELABS Company.

The transducer 6, situated inside the chamber 2, receives the fields resulting from the interaction between said specific excitation field and said substance 1. The transducer 6 transforms said resulting fields into electric signals. These electric signals arrive at the output terminals 9' of the transducer 6 under the form of a variable difference of potential or of an electric current of variable intensity. The transducer 6 comprises a bobbin with a soft iron core. This bobbin has an impedance of 300 ohms, an internal diameter of 6 mm, an external diameter of 16 mm, and a length of 6 mm. The magnetic core in soft iron is placed in contact with the external walls of the container 3.

Advantageously, the characteristic electric signals available at the output from the transducer 6 are amplified by a preamplifier 16. The amplifier-preamplifier 16 has the following specifications: passband from 10 Hz to 20 kHz, gain 50 to 100 for an input sensitivity of +/−100 mV or gain 500 to 2000 for an input sensitivity of +/−5 mV (to be used in the case of an "opposition series" connection of a second transducer). The characteristic electric signals can b e recorded 31, stored 33, transferred 11, 29, remotely by implementing technologies of electronics, computers and telecommunications known to those skilled in the art.

The recording of characteristic electric signals, or that of electric signals derived after amplification or processing, can be carried out in analog by a signal recorder, in particular o n magnetic tape, adapted to the frequencies of the characteristic electric signals at the output from the transducer 6. Since the passband used corresponds to the audio band, one can i n particular use a tape recorder. The output terminal 9' of the device for producing signals 10 is linked to the microphone input or to the line input of such a tape recorder. During play, the characteristic electric signals recorded are collected at an output terminal, in particular at the line output or at the loudspeaker output of the tape recorder. Preferably, digital recording of the characteristic electric signals is carried out after analog-digital conversion of said signals. In order to d o this, a micro-computer 17 is used, provided with a signal acquisition card 25. For example, one can use a PC 17 type computer, operating on the WINDOWS® 95 operating system from MICROSOFT. This microcomputer can be of the same type as that used to generate the excitation field. It can be the same microcomputer. In this case it comprises, apart from the sound card, an acquisition card 25, a microprocessor 27, an input/output interface 29, a controller 31, a mass storage 33 and a video interface 35 linked by one or several bus 37. The acquisition card 25 comprises a analog-digital converter 39 possessing, preferably, a resolution higher than 12 bits, and advantageously equal to 16 bits, as well as a sampling frequency double the maximum frequency one wishes to be able to digitise, for example 44 kHz. The output 9' of the transducer 6 is linked to the input 9 of the digital-analog converter 39 via the preamplifier 16.

All links consist of shielded cable. All the apparatus is earthed.

Advantageously, in order to process the characteristic electric signals or the signal derivatives, one uses the Matlab software from the company "The MathWorks". The output of the device 10 for producing characteristic electric signals is connected to the input 9 of the analog-digital converter 39 of the card 25 of the computer 17. One proceeds with a n acquisition of characteristic electric signals for a length of time for example of between 1 and 60 sec (for example 6 sec) and the digital file is saved in a mass storage 33, for example under the form of a sound file with the WAV format. This file can later undergo digital processing, as for example digital amplification for calibrating the signal level, filtering for eliminating unwanted frequencies, or be transformed into its spectrum by a discrete FOURIER transform, preferable by the algorithm of FFT "Fast Fourier Transform".

The time length of the signal produced can be increased by repeating several times in a file a fragment or the totality of the sound file originally produced.

These processing means of characteristic electric signals can be used to improve performances of said characteristic electric signals. In the case of a first embodiment variant, a second transducer of the first type described above is envisaged. This second transducer transforms the excitation field into electric signals, in the absence of said substance. These electric signals are subtracted by an opposition series connection to the signals derived from the first transducer. Thus one obtains signals more representative of the interaction between the specific excitation field and the substance. In the case of a second embodiment variant, the processing means take into account the characteristics of the specific excitation field and reprocess the characteristic electric signals in the following way. First of all one proceeds by calculating the spread of the PSD. Then this power spectral density is contracted by conserving only the frequency band ranging for example from 140 Hz to 14 kHz, and reconstituting a signal from this PSD and randomly generated phases, and finally calibrating the power of the signal thus produced.

The characteristic electric signals available at the exit of the output from the device constituted by the combination of the emitter 4, the transducer 6 and if applicable the preamplifier 16 already themselves constitute products suitable for industrial applications. They can be amplified, processed, saved, stored, transferred remotely by implementing state of the art technologies in electronics, computers and telecommunications. The industrial applications for which they can in particular be implemented have been noted.

The file of characteristic electric signals, recorded under digital form as has just been described, possibly after processing, can be transferred remotely by a computer communication network. This network can comprise radio links 11. The file of characteristic electric signals thus transmitted is recorded by the mass storage of the microcomputer 18. For example, one can use a computer of the PC type, operating on a WINDOWS® 95 operating system from MICROSOFT. This microcomputer 18 can be of the same type as that used for generating the excitation field. The file of characteristic signals thus transmitted and recorded can be exploited, in known ways, to produce analog characteristic electric signals. The possibly processed file is transformed by a digital-analog converter 41 of the card 25 (or a separate card) of the computer 18. The digital-analog converter 41 delivers analog electric signals to its output 8 characteristic of the biological activity of the substance from which they are issued. These signals can be transformed, as described below, into electromagnetic fields and applied to biological systems.

Referring to FIG. 1c, a description is given of an embodiment of a system making it possible to apply characteristic electric signals to a biological system receiver and to modify its chemical behaviour. The flask 50 contains the biological system receiver. This is constituted, for example, of 10 ml distilled water for an injectable preparation (Biosédra or other brands) in a 15 ml tube in polypropylene (Falcon, Becton Dickinson 2097). This flask is set in an electromagnetic field radiated by a transducer 51, typically a bobbin. The bobbin, for example, has a length of 120 mm, an internal diameter of 25 mm, an external diameter of 28 mm, with 631 turns of wire of 0.5 mm diameter and a resistance of 4 ohms. The bobbin 51 is earthed. Without this representing any limiting character, the bobbin 51 of the transducer has a vertical axis making it possible to introduce the flask 50 containing the receptor biological system. The input terminals 8' of this bobbin 51 are linked, in the case of the embodiment variant described, to the output 8 of the digital-analog converter 41 of the microcomputer 18 via an amplifier 19 with the following specifications: passband from 10 Hz to 20 kHz, gain 1 to 20, input sensitivity 250 mV, output power RMS 60 W under 8 ohms, signal to noise ratio 80 dB. The voltage at the terminals of the bobbin 51 has an amplitude of 5 Veff and the signal is applied for 10 minutes. The input terminals 8' of the applicator can also be, in the case of certain embodiment variants, directly connected to the output of the preamplifier 16 or to the output 8 of the digital-analog converter 41 of the computer 17.

The invention also relates to the methods making i t possible to control the correlation between on the one hand, said signal derived from the transducer 6 and on the other hand, the biological and/or chemical activity or the biological and/or chemical behaviour of said substance or said active element contained in said substance. This control is carried out by applying, by means of a transducer of the type described in reference to FIG. 1c, signals derived from the transducer 6 to a biological control system and verifying that said biological control system reacts in a specific manner to the signals derived from said first transducer. In the case where said signals are processed, it is these processed signals which are applied to said biological control system. The reaction of said biological control system must be in relation to the nature of the biological and/or chemical activity or the biological and/or chemical behaviour of said substance or said active element contained in said substance from which are issued the signals derived from said first transducer.

As an example of a biological control system, an d referring to FIG. 2, a test will be described below derived from that known under the test name of a perfused isolated guinea-pig heart (or Langendorff experiment) and whose process is described in the work entitled: "Methods in Immunology and Immunochemistry" published by Williams and Chase, Academic Press 1976, particularly page 68; or further in the work entitled: "L'experimentation animate en cardiologie" INSERM Médecine-Science—Coll. Flammarion—Author Bernard SWYNGHEDAUW—particularly Ch. 3.1 p.81 "Organe Isolé—Coceur Isolé selon Langendorff—Montage à pression coronaire constante"; or further in the work entitled "The isolated perfused Heart according to Langendorff" H. J. Döiring, H. Dehnart—Biomesstechnik—Verlag March GmbH, D-7806 March. In FIG. 2 one recognises the diagram known from the Langendorff experiment. The equipment described in these works has been completed by a transducer in the form of a bobbin 60 of a varnished copper wire of diameter 0.5 mm, with a diameter of 110 mm, a length of 40 mm and with an impedance of 4 ohms.

Three experiments were carried out with characteristic electric signals coming respectively from the following substances:

for the first, ionophoretic-calcium A 23187 (Sigma C-7522) (I) at a concentration of $10^{-6}M$ in distilled water for injectable preparation (for example the Biosedra brand).

for the second, distilled water for injectable preparation (for example the Biosedra brand). (E)

for the third, caffeine (Sigma C-0750) (C) at a concentration of $10^{-6}M$ in distilled water for injectable preparation (for example the Biosédra brand). (E)

For each of these three experiments, the substances were placed in the container 3 of the chamber 2 and their characteristic electric signals were acquired in conformity with the operating process described with reference to FIGS. 1, 1a and 1b.

The three characteristic electric signals produced as described above were applied to the guinea-pig heart, connecting the terminals 8' of the bobbin 60 to the output of the amplifier 19 of power 60 W. The three characteristic electric signals were applied for 2 minutes under a voltage of 5 Veff.

The fraction collector collected the tubes making it possible to measure the debit of the guinea-pig heart at the rate of 1 tube per minute. The buffer solution crossing the heart had the following composition: CaCl 2 mM, NaHCO3 25 mM, NaCl 118 mM, MgSO4 1.2 mM, KHPO4 1.2 mM, Glucose 11 mM, Pyruvate 2 mM.

The table below shows (in ml) the quantity of the buffer solution recuperated in the collector tubes during the time.

| Time mins. | No signal | Signal ionophoretic-calcium | Signal water | Signal caffeine |
|---|---|---|---|---|
| 1 | 4.4 | 4.4 | 4.5 | 4.3 |
| 2 | 4.3 | 4.3 | 4.5 | 4.4 |
| 3 | 4.3 | 4.4 | 4.4 | 4.4 |
| 4 | 4.4 | 4.3 | 4.5 | 4.5 |
| 5 | 4.4 | 4.2 | 4.5 | 4.2 |
| 6 | 4.3 | 4.9 | 4.4 | 4.0 |
| 7 | 4.3 | 5.2 | 4.4 | 3.6 |
| 8 | 4.4 | 5.4 | 4.5 | 3.4 |
| 9 | 4.3 | 5.4 | 4.5 | 3.2 |
| 10 | 4.4 | 5.2 | 4.4 | 3.0 |
| 11 | 4.3 | 5.0 | 4.5 | 3.0 |
| 12 | 4.4 | 5.0 | 4.4 | 3.2 |
| 13 | 4.3 | 4.8 | 4.4 | 3.4 |
| 14 | 4.4 | 4.8 | 4.5 | 3.6 |
| 15 | 4.3 | 4.6 | 4.4 | 3.8 |
| 20 | 4.3 | 4.5 | 4.4 | 4.0 |
| 25 | 4.3 | 4.5 | 4.5 | 4.1 |
| 30 | 4.3 | 4.5 | 4.4 | 4.0 |

This table shows that the guinea-pig heart reacted to the characteristic electric signals coming from ionophoretic-calcium, water and caffeine as it would have reacted to injections of each of these three substances (see table below).

| Time minutes | Water | ionophoretic-calcium $10^{-6}M$ | caffeine $10^{-6}M$ |
|---|---|---|---|
| 1 | 5.2 | 5.1 | 5.1 |
| 2 | 5.1 | 5.0 | 5.0 |
| 3 | 5.0 | 5.2 | 5.0 |
| 4 | 5.1 | 5.0 | 4.9 |
| 5 | 5.1 | 4.9 | 4.6 |
| 6 | 5.2 | 5.4 | 4.2 |
| 7 | 5.2 | 5.6 | 4.0 |
| 8 | 5.1 | 6.2 | 4.1 |
| 9 | 5.1 | 6.4 | 4.0 |
| 10 | 5.2 | 6.4 | 4.2 |
| 11 | 5.1 | 6.2 | 4.1 |
| 12 | 5.0 | 6.0 | 4.3 |
| 13 | 5.1 | 6.0 | 4.4 |
| 14 | 5.0 | 5.9 | 4.5 |
| 15 | 5.0 | 6.0 | 4.5 |
| 20 | 5.1 | 5.7 | 4.6 |
| 25 | 5.0 | 5.4 | 4.5 |
| 30 | 5.0 | 5.2 | 4.5 |

Next, as an example, a description follows with reference to FIGS. 3, 3a, 3c and 3d of a precipitation test between the polysaccharidic antigen of *Escherichia coli* K1 and an antibody against this antigen making it possible to control the characteristic electric signals of the biological activity of *Escheria coli*. This test is defined below under the name of precipitation test.

One tests the effects on a precipitation reaction between the polysaccharidic antigen of *Escherichia coli* K1 and an antibody directed against this antigen:

from the application of a characteristic electric signal of the biological activity of an antigenic substance foreign to this reaction such as the Streptococcus, from the application of a characteristic electric signal of the biological activity of the polysaccharidic antigen of *Escherichia coli,* from the simultaneous application of a characteristic electric signal of the biological activity of Streptococcus and the characteristic electric signal of the biological activity of an antibody directed against *Escherichia coli,* from the simultaneous application of a characteristic electric signal of the biological activity of *Escherichia coli* and the characteristic electric signal of the biological activity of a n antibody directed against this antigen.

The acquisition of the characteristic electric signals of the biological activities of *Escherichia coli*, of its specific antibody and of the polysaccharidic antigen of Streptococcus was carried out by means of the device 10 described with reference to FIGS. 1, 1a, 1b.

The acquisition of the characteristic electric signal of the biological activity of Streptococcus was carried out by placing at the centre of the chamber 2 a container 3 holding 1 ml of an aqueous suspension of Streptococcus bacteria previously formalised ($6.10^6$ cfu/ml).

The acquisition of the characteristic electric signals of the biological activity of the specific antibody of *Escherichia coli* and its specific antibody was carried out by operating in the same manner, but using respectively:

- a container 3 holding 1 ml of an aqueous suspension of bacteria of *Escherichia coli* K1 previously formalised ($6.10^6$ cfu/ml).
- a container 3 holding 1 ml of a suspension of particles of a latex sensitised by a mouse monoclonal antibody specific of *Escherichia coli* K1, coming from a PASTOREX® MENINGITIS kit (Ref. 61709—SANOFI DIAGNOSTICS PASTEUR).

The tests were carried out using as reagents:

- on the one hand, a solution of polysaccharidic antigen of *Escherichia coli* K1 prepared by dissolving an antigenic extract from a PASTOREX® MENINGITIS kit (Ref. 61709—SANOFI DIAGNOSTICS PASTEUR) in 1 ml of distilled and sterile water, then dilution to 1/7, 1/7.5 or 1/8 in physiological serum; and
- on the other hand the latex sensitised by a mouse monoclonal antibody specific of *Escherichia coli* K1 present in this same kit, after dilution to 1/3 in physiological serum.

For each of these tests, the following protocol was used:

- one places in an oven heated to 37° C. a transducer 151 constituted by a bobbin measuring 120 mm in length and 25 mm internal diameter, with 631 turns and a resistance of 4.7 ohms and linked by its input terminal 8' to the output 8 of the digital-analog converter of a Soundblaster card and a computer 17 (one could also use a computer 18 remotely) reinserting the recorded files constituted by the electric signals one wishes to apply for the time required to bring this transducer to the temperature of 37° C.;
- one deposits on a slide 147 supplied with a capillary 149 in a serpentine shape (of the type of those provided in the PASTOREX MENINGITIS kits), at a small distance from the opening of the latter, a drop 145 (40 to 50 µl) of the antigenic solution as described in point b) above, together with a drop 143 (also corresponding to a volume of 40 to 50 µl), latex sensitised by the antibody, taking care that these drops do not mix.
- one applies, to the two drops of reagents thus deposited, the electric signal or signals desired by placing the slide at the centre of the transducer 151 for about 2 minutes and reinserting a sound file with the aid of the computer 17 (or the remote computer 18),
- one mixes the two drops of reagents 143, 145 for about 10 seconds and then leaves the reaction mixture in the oven for about 13 minutes to migrate into the capillary and the precipitation reaction to take place:
- one takes the blade out of the oven and then proceeds to read this precipitation.

This reading is carried out by analysis, by means of analysis software and image processing on a PC type computer using the WINDOWS® 95 operating system (MICROSOFT), of an image acquired with the aid of a video camera positioned on an optical microscope and connected to said computer by a video acquisition card. The camera works in the grey shades. A first processing increases the contrast, the threshold being set so that the precipitates appear in black, while the zones without latex particles or precipitates appear white.

Based on the analysis of two-dimensional space spread of the dark zones of the image, the computer determines a precipitation index (I) calculated according to the formula:

$$I = \frac{\text{Surface area of precipitates of size} > 60 \text{ pixels}}{\text{Surface area of precipitates of size} = 60 \text{ pixels}}$$

The precipitation index is accordingly higher when the size of the precipitates formed during the precipitation reaction is greater. The control test for the presence of a characteristic signal of the biological activity of *Escherichia coli* is considered as positive when, during an experiment, the application of characteristic electric signals of the biological activity of *Escherichia coli* and/or the biological activity of its specific antibody leads to obtaining a precipitation index significantly higher (by at least 40%) than the maximum of those obtained, under the same conditions, and over for example 3 experiments, after application of the characteristic electric signal of the biological activity of Streptococcus.

Table A below shows the precipitation indexes obtained in a first series of tests aimed at comparing the effects of the application of characteristic electric signals of the biological activity of *Escherichia coli* (*E. coli*) coming from a biological system containing *Escherichia coli* with those observed after application, under the same reaction conditions, of characteristic electric signals of the biological activity of Streptococcus (St) coming from a biological system containing Streptococcus and for 3 different dilutions (1/7, 1/7.5 and 1/8) of the polysaccharidic antigen of *Escherichia coli* K1 used as reagent in the precipitation reactions.

TABLE A

| Dilution of the solution of | Precipitation index (I) | |
| --- | --- | --- |
| *E. coli* K1 antigen | Signal St | Signal *E. coli* |
| 1/7 | 11 | 173 |
|  | 6 | 52 |
|  | 16 | 154 |
| 1/7.5 | 58 | 141 |
|  | 32 | 117 |
|  | 12 | 107 |
| 1/8 | 10 | 113 |
|  | 6 | 37 |
|  | 8 | 21 |

Moreover, FIGS. 3a and 3b show, as examples, images of the precipitates formed, on the one hand, after application of the characteristic electric signal of the biological activity of Streptococcus (FIG. 3a) and, on the other hand, after application of the characteristic electric signal of the biological activity of *Escherichia coli* (FIG. 3b). These images correspond respectively to the precipitation indexes of 32 and 117 which are recorded on line 5 of Table A.

As for Table B below, the precipitation indexes obtained in a second series of experiments within the framework of which the effects of simultaneous application of the characteristic electric signal of the biological activity of *Escherichia coli* and the characteristic electric signal of the biological activity of the antibody directed against *Escherichia coli* were compared to those of the simultaneous application, under the same reaction conditions, of the characteristic electric signal of the biological activity of Streptococcus and of the characteristic electric signal of the biological activity of the antibody directed against *Escherichia coli*, carried out for 2 different dilutions (1/7 and 1/7.5) of the polysaccharidic antigen of *Escherichia coli* K1 used as reagent.

TABLE B

| Dilution of the solution of *E. coli* K1 antigen | Precipitation index (I) | |
|---|---|---|
| | Signal St + Signal antibody anti-*E. coli* | Signal *E. coli* + Signal antibody anti-*E. coli* |
| 1/7 | 18 | 94 |
| | 71 | 247 |
| 1/7.5 | 48 | 212 |
| | 93 | 1141 |

FIGS. 3c and 3d show, also as examples, images of precipitates corresponding respectively to the precipitation indexes 71 and 247 recorded on line 2 of Table B.

All these results demonstrate clearly the aptitude presented by a ligand/receptor couple for revealing and controlling the presence of a characteristic electric signal of the biological activity of a ligand and/or its receptor. In fact, in the presence of a specific characteristic signal of the ligand/receptor couple or one of the elements of this couple, the formation of complexes formed by the reaction between this ligand and this receptor is amplified. This amplification is very specific, since the characteristic electric signal of the biological activity of a biologically active element, but foreign to this reaction, does not itself produce this amplification effect.

In the meaning of the present invention, the "ligand/receptor couple" means any couple formed by two substances able to recognise each other specifically, to link together and to act together to form complexes. Thus, it can concern an antigen/antibody couple, or hapten/antibody in which the ligand (the antigen or the hapten) can be a biological compound (protein, enzyme, hormone, toxin, tumour tag), a chemical compound (toxic or medicated active principle, for example), or a cell or particle antigen (cell, bacteria, virus, fungus, . . . ), the receptor being able to be a soluble antibody or a membranous receptor. It can also be a couple formed by an enzyme and its specific substrate.

These results show clearly that it is possible to use ligand/receptor couples and, in general, test biological systems to constitute a correlation table between the characteristic signals issued from a determined substance or from an active element contained in a determined substance and the modifications they can induce on test biological systems, in particular such as a ligand/receptor couple.

These correlation tables can be used later for detecting active elements by analysing the effects of characteristic signals coming from them on test biological systems recorded in the correlation table.

As an example, with reference to FIG. 4, a presentation is given below of the test known under the name of guinea-pig cutaneous test and described in chapter 11 (p.346–351) in the second edition of "Immunology" edited by Jean-Francois Bach, coll. John Wiley & Sons; or further in the 3rd edition of "The handbook of Experimental Immunology" edited by D. M. Weir, coll. Blackwell, Ch. 21 "Passive cutaneous anaphylaxis (PCA)" by W. E. Brocklehurst; or further in the work edited by Williams & Chase entitled "Methods in IMMUNOLOGY and IMMUNOCHEMISTRY"—Vol. 5—Ch. 19 "Anaphylaxis".

The guinea-pig is used when still alive, and is given a n intravenous injection of a blue colorant (Evans blue—Sigma E 2129) which fixes on the blood albumin. The albumin does not leave the vessels, unless there is inflammation, and thus vasodilatation and permeability of the vessels, the typical example of such a reaction with man being urticaria.

The test is carried out by injecting under the skin of the animal prepared in this way, 0.1 ml of the solution whose activity is to be controlled. Nextone measures the diameter of the blue marks appearing around the points of injection. In order to do this the skin is scanned, and then the bitmap image file is recorded. Finally the sizes of the blue marks due to the reaction are evaluated.

In the example described, a control was carried out of the presence of signals characteristic of the biological activity of the acetylcholine neuromediator (ACh; Sigma A2661) in solution in a physiological solution, by analysing the effects o n the skin of a guinea-pig:

on the one hand, of an injection of 0.1 ml distilled water, after applying to this distilled water a characteristic electric signal of the biological activity of acetylcholine, on the other hand, of an injection of 0.1 ml distilled water, after applying to this distilled water a characteristic electric signal of the biological activity of a product close to acetylcholine but inactive: the mixture acetate/choline (A-C) (A: Sigma S8625; C: Sigma C7017).

The acquisition of the characteristic electric signals of the biological activities of acetylcholine and the acetate/choline mixture was carried out by means of the device 10 described with reference to FIGS. 1, 1a, 1b.

The acquisition of the characteristic electric signal of the biological activity of acetylcholine was carried out by placing in the centre of the chamber 2 a container 3 holding 1 ml of a solution of acetylcholine in distilled water at the concentration of $10^{-6}$M.

The acquisition of characteristic electric signals of the biological activity of the mixture acetate/acetylcholine was carried out by operating in the same manner, but using a container 3 holding 1 ml of a solution of acetate/acetylcholine in distilled water at the concentration of $10^{-6}$M.

For each of the tests, the following protocol was used:
The bobbin 51 of FIG. 1c was used as applicator.
The numbers figuring in the first column of tables C, D and E below correspond to the references in FIG. 4.

TABLE C

| No. | Distilled water solution injected | Dia. in mm |
|---|---|---|
| 200 | After application | 12 |
| 201 | of the ACh signal | 6 |
| 202 | | 7 |
| 203 | | 7 |
| 204 | | 16 |
| 300 | Without application | 3 |
| 301 | of the signal | 2 |
| 302 | | 4 |
| 303 | | 3 |
| 304 | | 1 |

TABLE C-continued

| No. | Distilled water solution injected | Dia. in mm |
|---|---|---|
| 305 | | 0 |
| 306 | | 1 |

Experiments numbered 200 to 204 show that the solutions of distilled water injected after application of the ACh signal setoff a significant cutaneous reaction (average 11 mm) compared with the same solutions of distilled water injected without application of the ACh signal. The latter d o not setoff a reaction as shown in experiments numbered 300 to 306 (3 mm).

TABLE D

| No. | Solution injected | Dia. in mm |
|---|---|---|
| 310 | ACh in $10^{-6}$M solution | 23 |
| 311 | | 25 |
| 312 | | 23 |
| 313 | | 21 |
| 314 | | 18 |

Comparison of the experiments in tables C and D shows that the injections of solutions of distilled water after application of the ACh signal (experiments 200 to 204) have effects which are less, but comparable, on the guinea-pig skin to those of injections of ponderal ACh solutions (experiments 310 to 314).

TABLE E

| No. | Distilled water solution injected | Dia. in mm |
|---|---|---|
| 400 | After application | 2 |
| 401 | of the A-C signal | 2 |
| 402 | | 1 |
| 403 | | 3 |
| 404 | | 1 |
| 410 | A-C in solution at $10^{-6}$M | 3 |
| 411 | | 2 |
| 412 | | 1 |

Experiments numbered 400 to 404 and 410 to 412 in Table E are carried out from a product close to acetylcholine but inactive: the acetate/choline (A-C) mixture.

Experiments 410, 411, 412, correspond to an injection of a ponderal solution of A-C $10^{-6}$M. One notes that an injection of distilled water solution after application of the A-C signal (exp. 400 to 404) and that a ponderal injection (exp. 410, 411, 412) do not provoke any effect (diameter between 1 and 3 mm). These injections show that the cutaneous reaction of the guinea-pig is really specific to the nature of the substance in solution because these injections, carried out under the same conditions as the injections numbered 200 to 202, have no effect.

The experiments of tables C to E make it evident that the guinea-pig skin test makes it possible to control the presence of a signal coming from a substance with a biological activity such as acetylcholine.

Below is described the method used for controlling the following homeopathic products: arnica 7CH, acetylcholinum 7CH.

First of all one has to produce the characteristic signals of the product to be tested. In the case where the homeopathic product to test is a solution, one proceeds by registering a sample of 1 ml as described in this patent. In the case where one wishes to test homeopathic granules, first of all a solution is prepared, for example 5 ml, by diluting 2 granules per ml of distilled water for injectable preparation (for example the Biosédra brand), and then one proceeds with the registering of a sample of 1 ml according to the method described in this patent.

Nextone uses for example one or several of the three methods described above (perfused isolated guinea-pig heart; precipitation test of a ligand/receptor couple and cutaneous test on a guinea-pig). Since the correlation between the reaction of these biological control systems and the biological and/or chemical activity of the product having served to produce the homeopathic product has been demonstrated, a positive reaction of the biological control system will show the presence of the activity searched for in the homeopathic product tested. In the same way, a negative reaction of the biological control system will show the absence of the activity searched for in the homeopathic product tested.

| Product to be tested | Result on the skin of a guinea-pig (diameter of marks in mm) | Detection of activity |
|---|---|---|
| Neutral granules | 0.6 ± 0.5 (n = 5) | NO |
| Arnica 7CH granules | 16.6 ± 2.9 (n = 5) | YES |

What is claimed is:

1. Method for producing from a substance (1) signals, in particular electric signals, characteristic of the biological and/or chemical activity or of the biological and/or chemical behaviour of said substance or of an active element contained in said substance; said method comprising the stages:
    of placing said substance in a zone (2) submitted to a specific excitation field of electric, magnetic and/or electromagnetic nature (4), said specific excitation field having the characteristic of having a power spectral density spread over a frequency band, particularly of the white noise type or of the pink noise type;
    said method also comprising:
        of transforming the resulting fields from the interaction of the specific excitation field of the substance into signals, in particular electric signals, by means of a first transducer (6) receiving said resulting fields,
        said signals being characteristic of the biological and/or chemical activity or of the biological and/or chemical behaviour of said substance or said active element contained in said substance.

2. Method according to claim 1 further comprising the stage
    processing (17) said signals derived from said first transducer (6) in function of second signals derived from a second transducer receiving the specific excitation field, in the absence of said substance or an active element contained in said substance,
in such a way that said processed signals are advantageously characteristic of the biological and/or chemical activity or of the biological and/or chemical behaviour of said substance or said active element contained in said substance.

3. Method according to claim 1 further comprising the stage:
    of processing (17) the signals derived from said first transducer, in function of the characteristics of the specific excitation field,
in such a way that said processed signals are advantageously characteristic of the biological and/or chemical activity or of the biological and/or chemical behaviour of said substance or said active element contained in said substance.

4. Method according to claim 1, said specific excitation field having a power spectral density such that, in the absence of said substance or an active element contained in said substance, the power spectral density of the signals produced by said first transducer of produced by an opposition series connection of said first and second transducers is uniform.

5. Method according to claim 1, said specific excitation field being generated by a sinusoidal signal generator of variable frequency with time and scanning a frequency band.

6. Method according to claim 5, said frequency band being in a frequency range lower than 100 kHz.

7. Method according to claim 1, said specific excitation field having the characteristic of having a uniform power spectral density over a band of frequencies, in such a way that said substance will be submitted to a neutral excitation field of white noise type.

8. Method according to claim 1, such that:
the zone (2) submitted to the specific excitation field is isolated from parasitic fields coming from the environment.

9. Method according to claim 1 further comprising the stage:
of applying, by means of a third transducer (51, 151) to a receptor biological system said signals derived from said first transducer (6) or the processed signal, in such a way that the biological and/or chemical activity or the biological and/or chemical behaviour of the receptor biological system will be modified in function of the nature of the biological and/or chemical activity or the biological and/or chemical behaviour of said substance.

10. Method according to claim 9, further comprising the stage:
of controlling the correlation between, on the one hand the signal derived from said first transducer (6) or the processed signal, and on the other hand the biological and/or chemical activity or the biological and/or chemical behaviour of said substance or said active element contained in said substance, by applying, by means of said third transducer (51, 151), the signal derived from the first transducer (6) or the processed signal to a biological control system and verifying that said biological system reacts in a specific manner to the signal derived from said first transducer or to the processed signal, according to the nature of the biological and/or chemical activity or the biological and/or chemical behaviour of said substance or said active element contained in said substance from which is issued the signal derived from said first transducer or the processed signal.

11. Method according to claim 10, such that the biological system is an isolated guinea-pig heart.

12. Method according to claim 10, such that the biological system is a ligand/receptor couple particularly an antigen/antibody couple.

13. Method according to claim 10, such that the biological system is an injectable substance provoking cutaneous reactions.

14. Method according to claim 10, such that the biological system is composed of isolated cells or cells in culture.

15. Method according to claim 1, such that said substance contains an active element in low or very low concentration.

16. System for producing signals, particularly electric signals, characteristic of the biological and/or chemical activity or the biological and/or chemical behaviour of substance (1) or an active element contained in said substance and system for implementing the properties of such signals, said system comprising:
an emitter (4) generating a specific excitation field of electric, magnetic and/or electromagnetic nature in a zone (2, 3) where said substance is situated; said specific excitation field having the characteristic of having a power spectral density spread over a frequency band, particularly of the white noise type or of the pink noise type;

said method also comprising:
a first transducer (6) receiving the resulting fields from the interaction of said specific excitation field and said substance, said first transducer transforming said resulting fields into signals, particularly electric signals, said signals being characteristic of the biological and/or chemical activity or the biological and/or chemical behaviour of said substance or said active element contained in said substance,
means of emission (51, 151) for applying said signals derived from said first transducer to a receptor biological system, in such a way that the biological and/or chemical activity or the biological and/or chemical behaviour of the receptor biological system will be modified in function of the nature of the biological and/or chemical activity or the biological and/or chemical behaviour of said substance.

17. System according to claim 16 further comprising:
means (17) for processing said signals derived from said first transducer (6), in function of the signals derived from a second transducer receiving the specific excitation field, in the absence of said substance or an active element contained in said substance,
so that said processed signals are advantageously characteristic of the biological and/or chemical activity or the biological and/or chemical behaviour of said substance or said active element contained in said substance.

18. System according to claim 16 further comprising:
means (17) for processing the signals derived from said first transducer (6), in function of the characteristics of the specific excitation field,
so that said processed signals are advantageously characteristic of the biological and/or chemical activity or the biological and/or chemical behaviour of said substance or said active element contained in said substance.

19. System according to claim 16 such that said emitter generates a specific excitation field with a power spectral density such that, in the absence of said substance or an active element contained in said substance, the power spectral density of the signals produced by said first transducer or produced by an opposition series connection of said first and second transducers is uniform.

20. System according to claim 16 such that said emitter generating said specific excitation field comprises a sinusoidal signal generator of frequency variable with time and sweeping a frequency band.

21. System according to claim 20, such that said frequency band is in a frequency range lower than 100 kHz.

22. System according to claim 16, said specific excitation field having the characteristic of having a uniform power spectral density over a frequency band.

23. System according to claim 16, such that it further comprises:
means (2) for isolating said zone from parasitic fields from the environment.

24. System according to claim 16, further comprising means of control for controlling the correlation between, on the one hand, the signal derived from said first transducer or the processed signal and, on the other hand, the biological and/or chemical activity or the biological and/or chemical behaviour of said substance or said active element contained in said substance, said means of control comprising a third transducer (51, 60, 151) applying the signal derived from said first transducer or the processed signal to a biological control system, said means of control further comprising means for verifying that the biological control system reacts in a specific manner to the signal derived from first transducer or the processed signal, according to the nature of the biological and/or chemical activity or the biological and/or chemical behaviour of said substance or said active element contained in said substance from which is issued the signal derived from said first transducer or said processed signal.

25. System according to claim 24, such that the biological control system is an isolated guinea-pig heart (FIG. 2).

26. System according to claim 24, such that the biological control system is a ligand/receptor couple particularly an antigen/antibody couple (FIG. 3).

27. System according to claim 24, such that the biological control system is an injectable substance provoking cutaneous reactions (FIG. 4).

28. System according to claim 24, such that the biological control system is composed of isolated cells or cells in culture.

29. System according to claim 16, such that said substance contains an active element in low or very low concentration.

30. Device for producing signals, particularly electric signals, characteristic of the biological and/or chemical activity or the biological and/or chemical behaviour of a substance or an active element contained in said substance, said device comprising:

an emitter (4) generating a specific excitation field of electric, magnetic and/or electromagnetic nature in a zone where said substance is situated, said specific excitation field having the characteristic of having a power spectral density spread over a frequency band, particularly of the white noise type or of the pink noise type;

said method also comprising:

a first transducer (6) receiving the resulting fields from the interaction of said specific excitation field and said substance, said first transducer transforming said resulting fields into signals, particularly electric signals, said signals being characteristic of the biological and/or chemical activity or the biological and/or chemical behaviour of said substance or said active element contained in said substance.

31. Device according to claim 30 further comprising:

means (17) for processing the signals derived from said first transducer, in function of the signals derived from a second transducer receiving the specific excitation field, in the absence of said substance, so that said processed signals are advantageously characteristic of the biological and/or chemical activity or the biological and/or chemical behaviour of said substance or said active element contained in said substance.

32. Device according to claim 30 further comprising:

means (17) for processing the signals derived from said first transducer, in function of the characteristics of the specific excitation field so that said processed signals are advantageously characteristic of the biological and/or chemical activity or the biological and/or chemical behaviour of said substance or said active element contained in said substance.

33. Device according to claim 30 such that said emitter generates a specific excitation field with a power spectral density such that, in the absence of said substance or an active element contained in said substance, the power spectral density of the signals produced by said first transducer or produced by an opposition series connection of said first and second transducers is uniform.

34. Device according to claim 30 such that said emitter generating said specific excitation field comprises a sinusoidal signal generator of frequency variable with time and sweeping a frequency band.

35. Device according to claim 34, such that said frequency band is in a frequency range lower than 100 kHz.

36. Device according to claim 30, said specific excitation field having the characteristic of having a uniform power spectral density over a frequency band.

37. System according to claim 30, such that it further comprises:

means (2) for isolating said zone from parasitic fields from the environment.

38. Application of the method, system or device according to claim 1 to the production of active substances particularly to the production of drugs; said active substances being produced by applying said signals derived from said first transducer (6) or said processed signals to a carrier substance.

39. Application of the method, system or device according to claim 1 to establishing a correlation table between the characteristic signals issued from a determined substance or from an active element contained in said determined substance and the modifications they can induce on test biological systems.

40. Correlation table established in conformity with claim 39.

41. Utilisation of the correlation table according to claim 40, for the detection of said determined substance or said active element contained in said determined substance, particularly remotely, after transmission of said characteristic signal to a testing laboratory possessing said test biological systems.

42. Utilisation of the correlation table according to claim 41, to control the production of homeopathic products.

43. Signal linked to a biological and/or chemical activity, obtained by means of a method according to claim 1.

44. Signal linked to a biological and/or chemical activity, obtained by means of a system according to claim 16.

45. Signal linked to a biological and/or chemical activity, obtained by means of a device according to claim 30.

\* \* \* \* \*